United States Patent [19]

Chen et al.

[11] Patent Number: 4,477,389

[45] Date of Patent: Oct. 16, 1984

[54] POLYHALOGENATED PHENYL ISOCYANATE SYNTHESIS WITH EXCESS PHOSGENE AND EITHER TRIETHYLAMINE OR TETRAMETHYLUREA

[75] Inventors: George C. Chen; Roger M. Rowell, both of Madison, Wis.

[73] Assignee: The United States of America as represented by the Secretary of Agriculture, Washington, D.C.

[21] Appl. No.: 436,542

[22] Filed: Oct. 25, 1982

[51] Int. Cl.³ .......................................... C07C 118/02
[52] U.S. Cl. ...................... 260/453 PH; 260/453 AR
[58] Field of Search .................................. 260/453 PH

[56] References Cited

U.S. PATENT DOCUMENTS

| | | | |
|---|---|---|---|
| 2,362,648 | 11/1944 | Lichty et al. | 260/453 PH |
| 2,689,861 | 9/1954 | Thompson | 260/453 PH |
| 2,915,545 | 12/1959 | Tazuma | 260/453 AR |
| 2,945,875 | 7/1960 | Tazuma | 260/453 AR |
| 3,201,433 | 8/1965 | Manes et al. | 260/453 P |
| 3,277,137 | 10/1966 | Powers | 260/453 AR |
| 3,277,138 | 10/1966 | Holtschmidt et al. | 260/453 AR |
| 3,305,574 | 2/1967 | Zecher et al. | 260/453 AR |
| 3,360,539 | 12/1967 | Henry | 260/453 AR |
| 3,449,397 | 6/1969 | Twelves | 260/453 PH |
| 3,467,689 | 9/1969 | Veniceriu et al. | 260/453 PH |

*Primary Examiner*—Dolph H. Torrence
*Attorney, Agent, or Firm*—M. Howard Silverstein; David G. McConnell

[57] ABSTRACT

Two procedures are described that can be used to prepare polyhalogenated phenyl isocyanates (2,4,6-trichloro,2,3,5,6-tetrachloro, pentachloro, 2,4,6-tribromo and 2,4,6-trifluoro derivatives) from the corresponding anilines in good yields (95–99%) with small amounts of urea byproducts (1–5%) within reasonable reaction times (3–6 hours). These are:

1. Liquid phase phosgenation of polyhalogenated anilines with tertiary amines as a hydrogen chloride acceptor.
2. Liquid phase phosgenation of polyhalogenated anilines in excess phosgene at the beginning and throughout the reaction.

8 Claims, No Drawings

POLYHALOGENATED PHENYL ISOCYANATE SYNTHESIS WITH EXCESS PHOSGENE AND EITHER TRIETHYLAMINE OR TETRAMETHYLUREA

FIELD OF THE INVENTION

This invention relates to the preparation of polyhalogenated phenyl isocyanates. More particularly, it relates to procedures in which polyhalogenated aromatic isocyanates are prepared by reacting the corresponding polyhalogenated aromatic amine with excess phosgene in an inert organic liquid diluent; and still more particularly, it relates to a great improvement in yield of the corresponding polyhalogenated aromatic isocyanates carrying out the amine-phosgene reaction in the presence of a large excess of phosgene and a specific amount of either triethylamine or tetramethylurea.

BACKGROUND OF INVENTION

The general reaction of an aromatic amine with phosgene to obtain the corresponding aromatic isocyanate was first reported in 1844 by Hentschel in Berichte, 17, 1284. Various publications and patents have improved this process over the years since this first report.

The addition of a halogen molecule to the amine aromatic ring has the effect of deactivating the amine in its conversion with phosgene to the corresponding isocyanate. Because of this, the original phosgene technology had to be modified to synthesize polyhalogenated aromatic isocyanates.

The patent to Thompson No. 2,689,861 relates to the preparation of trihalogenated phenyl isocyanates by reacting the corresponding aromatic amine with phosgene in the presence of a minor amount of tetramethylurea However, reinvestigation of the process described in this patent reveals that it is not an effective procedure for preparing trihalogenated phenyl isocyanates because the tetramethylurea used as a weak organic base, promotes the formation of urea byproduct derivatives, thus reducing the yield of tri-halogenated phenyl isocyanate. Furthermore, the process described in the above-mentioned patent is not suitable in the preparation of tetra and pentahalogenated phenyl isocyanates.

The patent to Lichty et al. No. 2,362,648 relates to the preparation of isocyanates by reacting the corresponding amine with phosgene in the presence of a small amount of tertiary amine as catalyst. However the patent fails to disclose the method as feasible in preparing polyhalogenated phenyl isocyanates.

SUMMARY OF THE INVENTION

An object of the present invention is to overcome the deficiencies and drawbacks of the prior art.

Another object of this invention is to synthesis polyhalogenated phenyl isocyanates in high yield.

Another object of this invention is to synthesize polyhalogenated phenyl isocyanates in high yield by reacting the corresponding polyhalogenated aromatic amine with excess phosgene in an inert organic liquid diluent.

A further object of this invention is the synthesis of polyhalogenated phenyl isocyanates in high yield by carrying out the amine-phosgene reaction in the presence of a large excess of phosgene and a specific amount of triethylamine as a catalyst.

A still further object of this invention is the synthesis of polyhalogenated phenyl isocyanates in high yield by carrying out the amine-phosgene reaction in the presence of a large excess of phosgene and a specific amount of tetramethylurea as catalyst.

DETAILED DESCRIPTION OF EMBODIMENTS

In the reaction of a polyhalogenated phenyl amine with phosgene catalyzed with an organic base, three products can result: the corresponding isocyanate, a byproduct urea derivative, and polymerization products. Formation of the byproduct urea decreases the yield of the desired isocyanate. If the reaction conditions are such that polymerization of the isocyanate occurs, the yield of the isocyanate is also reduced.

The results of this invention have shown that a stronger organic base catalyst such as triethylamine promotes the isocyanate formation, without subsequent polymerization, while the weaker organic base catalyst, tetramethylurea, promotes the formation of the byproduct urea derivatives, greatly reducing the yield of the desired isocyanate.

This tendency of the weaker base, tetramethylurea, to promote the formation of the undesirable byproduct urea derivative can be almost completely eliminated by starting the reaction of the polyhalogenated phenyl amine with an excess of phosgene and continuing the phosgene addition throughout the reaction. The amount of tetramethylurea used in the reaction is not important so long as it is above a minimum concentration of approximately 0.013 mole per mole of starting amine. Thus, tri-, tetra-, and pentahalogenated phenyl isocyanates have successfully been synthesised by:

(1) reacting 1 mole of the corresponding polyhalogenated phenyl amine with a saturated solution of phosgene and continuous addition of phosgene throughout the reaction in the presence of 0.015 to 1 mole equivalent of tetramethylurea.

A superior catalyst to tetramethylurea are the tertiary amines such as triethylamine. An almost quantitative yield of isocyanate with only minor amounts of urea byproduct is achieved using an 8-mole excess of phosgene and 2 moles of triethylamine. The triethylamine acts as a hydrogen chloride acceptor forming a stable amine salt which does not catalyze the isocyanate formed during the reaction to the byproduct urea:

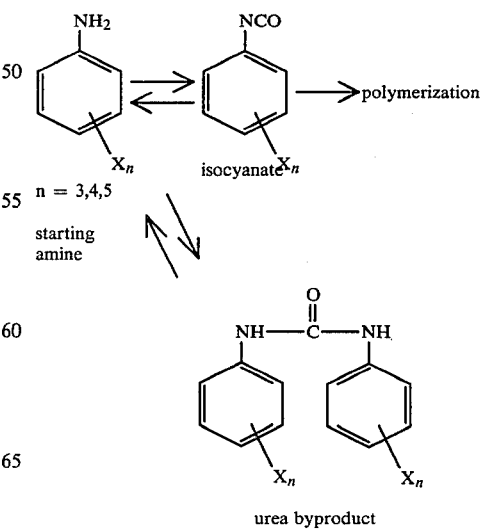

urea byproduct

-continued

X = halogen

Tetrahalogenated phenyl isocyanates have successfully been synthesized by (2) reacting 1 mole of the corresponding polyhalogenated phenyl amine with 8-mole equivalence of phosgene with 2-mole equivalence of triethylamine.

The invention is further illustrated by reference to the following examples.

PROCEDURE I, EXAMPLE I 2,4,6-Trichlorophenyl isocyanate (1). 1,1,3,3-tetramethylurea (1.52 ml, 12.75 mmoles) was added to a solution of phosgene (50.0 g, 505.43 mmoles) dissolved in toluene (150 ml). The resulting solution was stirred for 10 min. at which time 2,4,6-trichloroaniline (10.0 g, 50.90 mmoles) was added. The solution was heated to a temperature of 70°–80° C. for 1.5 hr. and then refluxed for 1.5 hr. while phosgene was bubbled in. After removing excess phosgene under reduced pressure, the clear upper layer solution was collected by decantation from the bottom oil layer, and the bottom oil layer was discarded. The solution was then evaporated to give a solid. The solid was dried under a vacuum to give a white solid (11.3 g, 99.3 pct). This product was recrystallized from dry carbon tetrachloride to give a colorless crystalline compound, m.p. 65°–66° C.; Infrared (IR): $\gamma$ max 2,282 cm$^{-1}$ (NCO); nuclear magnetic resonance (NMR) (chloroform-d): $\tau$, 2.7 (2-proton singlet, H-3,5, aromatic protons).

Anal. Calc. for $C_7H_2NOCl_3$: C, 37.79; H, 0.91; N, 6.30. Found C, 37.74; H, 1.00; N, 6.31.

EXAMPLE II 2,3,5,6-Tetrachlorophenyl isocyanate (2). 1,1,3,3-tetramethylurea (3.85 ml, 32.2 mmoles) was added to a solution of phosgene (70.2 g, 709.63 mmoles) dissolved in toluene (300 ml). The resulting solution was stirred for 30 min. at which time 2,3,5,6-tetrachloroaniline (20.0 g, 86.61 mmoles) was added. The solution was heated to temperatures of respectively 45°–50° C. and 80°–85° C., for 2 hr., and then refluxed for 1.5 hr. while phosgene was bubled in. After removing excess phosgene under reduced pressure, the clear upper layer solution was collected by decantation from the bottom oil layer, and the bottom oil layer was discarded. The solution was then evaporated to give a solid. The solid was dried under vacuum to give a white solid (22.1 g, 99.2 pct). The NMR spectrum of the products failed to show the existence of any amino protons, thus indicating a complete conversion of 2,3,5,6-tetrachloroaniline to 2,3,5,6-tetrachlorophenyl isocyanate. Additionally, the IR spectrum of the products showed a strong isocyanate (2,276 cm$^{-1}$) absorption and a trace of urea carbonyl (1,655 cm$^{-1}$) absorption. The product (1 g) was then dissolved in dry hexane and the insoluble solid was removed by filtration. The filtrate was evaporated to give a white solid. Thin layer chromatography (TLC) revealed that the filtrate is mainly the isocyanate product with a trace of the urea byproduct. The product (1 g) was recrystallized from dry hexane to give 2 white shiny needles (0.44 g, 43.5 pct), m.p. 62.5-63.5; IR: $\gamma$ max 2,276 cm$^{-1}$ (NCO); NMR (chloroform-d): $\tau$, 2.6 (1-proton singlet, H-4, aromatic proton).

Anal. Calc. for $C_7HNOCl_4$: C, 32.72; H, 0.39; N, 5.45. Found: C, 32.85; H, 0.31; N, 5.37

EXAMPLE III

Pentachlorophenyl isocyanate (3). 1,1,3,3-tetramethylurea (1.8 ml, 15.05 mmoles) was added to a solution of phosgene (87.0 g, 879.45 mmoles) dissolved in toluene (300 ml). The resulting solution was stirred for 30 min. at which time pentachloroaniline (15.0 g, 56.53 mmoles) was added. The solution was heated to a temperature of 80°–83° C. for 6 hr. while phosgene was bubbled in. After removing excess phosgene under reduced pressure, the clear upper layer solution was collected by decantation from the bottom oil layer, and the bottom oil layer was discarded. Additionally, the bottom layer solution containing the oil layer and the precipitate was filtered. The oil layer was separated from solution by a separatory funnel and discarded. The solution was then evaporated to give a solid. The solid was dried under vacuum to give a white solid (16.4 g, 99.8 pct). The NMR spectrum of the product showed no amino protons indicating a complete conversion of pentachloroaniline to pentachlorophenyl isocyanate. Additionally, the IR spectrum of the product showed a strong isocyanate (2,280 cm$^{-1}$) absorption and a trace of urea carbonyl (1,655 cm$^{-1}$) absorption. The product (1 g) was then dissolved in dry hexane and the insoluble solid was removed by filtration. The filtrate was evaporated to give a while solid. TLC showed the filtrate is mainly the isocyanate product with a trace of byproduct urea. The solid was recrystallized from dry hexane to give 3 white shiny flakes (0.59 g, 59.2 pct), m.p. 100.5°–102° C. (lit. m.p. 99°–101° C.); IR: $\gamma$ max 2,280 cm$^{-1}$ (NCO).

Anal. Calc. for $C_7NOCl_5$: C, 28.86; N, 4.81. Found: C, 28.75; N, 4.74.

EXAMPLE IV 2,4,6-Triflorophenyl isocyanate (4). 1,1,3,3-tetramethylurea (0.9 ml, 7.52 mmoles) was added to a solution of phosgene (28.06 g, 283.65 mmoles) dissolved in benzene (80 ml). The resulting solution was stirred for 10 min. at which time 2, 4,6-trifluoroaniline (4.4 g, 30.00 mmoles) was added. The solution was heated to a temperature of 60° C. for 2 hr. and then refluxed for 1 hr. while phosgene was bubbled in. After removing excess phosgene under reduced pressure, the clear upper layer solution was collected by decantation from the bottom oil layer, and the bottom oil layer was discarded. The solution was evaporated to give a yellow liquid (6.8 g, 131 pct). The liquid was distilled to give an azeotopic mixture, b.p. 80°–134° C.; IR: max 2,276 cm$^{-1}$ (NCO); NMR (chloroform-d); 3.40, 3.27, 3.14 (2-proton triplets, H-3,5, aromatic protons), 2.70 (6-proton signlet, benzene).

Attempts to prepare 2,4,6-trifluorophenyl isocyanate using a low boiling solvent, dichloromethane, were unsuccessful. The liquid, after removing solvent, was distilled to give a distillate having a boiling range of 140°–147° C. The NMR spectrum of the distillate showed an azeotropic mixture of 2,4,6-trifluorophenyl isocyanate and dichloromethane. An azeotropic mixture also resulted using toluene as a solvent.

EXAMPLE V 2,4,6-Tribromophenyl isocyanate (5), 1,1,3,3-tetramethylurea (1.95 ml, 16.34 mmoles) was added to a solution of phosgene (51.2 g, 517.56 mmoles) dissolved in toluene (300 ml). The resulting solution was stirred for 30 min. at which time 2,4,6-tribromoaniline (20.0 g, 60.60 mmoles) was added. The solution was heated to a temperature of 45°–50° C. for 2 hr, and then to a temperature of 80°–85° C. for 2 hr, while phosgene was bubbled in. After removing excess phosgene under reduced pressure, the clear upper layer solution was collected by decantation from the bottom layer, and the bottom oil layer was discarded. The bottom or oil layer of the solution was also filtered. The precipitate was disubstituted urea (1,656 cm$^{-1}$). The oil layer was separated from the rest of solution by a separatory funnel and then discarded. The solution was evaporated to give a solid which in turn was dried under vacuum to give a white solid (21.13 g, 98.01 pct). The NMR spectrum of the product showed no amino protons which indicated a complete conversion of 2,4,6-tribromoaniline to 2,4,6-tribromophenyl isocyanate. The IR spectrum of the product showed a strong isocyanate (2,270 cm$^{-1}$) absorption and a trace of urea carbony (1,656 cm$^{-1}$) absorption. The product (1 g) was dissolved in dry hexane and the insoluble solid was then filtered off. The remaining filtrate was evaporated to give a white solid. The solid was recrystallized from dry hexane to give a white powder (0.62 g, 62.4 pct), m.p. 91.5°–93° C.; IR: $\gamma$ max 2,270 cm$^{-1}$ (NCO); NMR (chloroform-d): $\tau$ 2.37 (2-proton singlet, H-3,5, aromatic protons).

Anal. Calc. for $C_7H_2NOBr_3$: C, 23.63; H, 0.57; N, 3.94. Found: C, 23.65; H, 0.56; N, 3.94.

PROCEDURE II, EXAMPLE I 2,3,5,6-Tetrachlorophenyl isocyanate (6). Triethylamine (2.78 ml, 0.02 mmoles) was added to a solution of phosgene (7.92 g, 0.08 mmoles; purified by passing through cottonseed oil and concentrated sulfuric acid) dissolved in 1,2-dichloroethane (80 ml). The resulting solution was stirred for 10 min. at which time 2,3,5,6-tetrachloroaniline (2.31 g, 0.01 mmoles was added. The solution was then refluxed for 4 hr. and completely evaporated to give a solid. The solid was dried under vacuum to give a white solid. The NMR spectrum of the product showed no amino protons which indicated complete conversion of 2,3,5,6-tetrachloroaniline to 2,3,5,6-tetrachlorophenyl isocyanate. A complete conversion of the amine to the isocyanate was reached after 3-hr. reflux. The IR spectrum of the product showed a strong isocyanate (2,276 cm$^{-1}$) absorption and a trace urea carbonyl (1,665 cm$^{-1}$) absorption. The product can be purified by dissolving it in dry hexane and crystallizing the concentrated filtrate to give a 98 percent yield of white needles, m.p. 62.5°–63.5° C.; IR: $\gamma$ max 2,276 cm$^{-1}$ (NCO); NMR (chloroform-d): $\tau$ 2.6 (1-proton singlet, H-4, aromatic proton).

Anal. Calc. for $C_7HNOCl_4$: C, 32.72; H, 0.39; N, 5.45. Found: C, 32.85; H, 0.31; N, 5.37.

It is to be understood that the invention is not limited to the embodiments disclosed which are illustratively offered and that modifications may be made without departing from the invention. For example, while the catalysts triethylamine and tetramethylurea have been set forth as examples, it will be understood that other closely related compounds may be used in their place selected from tri (lower alkyl) amine and tetra (lower alkyl) urea wherein "lower alkyl" includes 1–4 carbons, it being understood further that the alkyls may be different lower alkyls; for example, dimethylethylamine could be used as a catalyst.

We claim:

1. A method for preparing a tri-, tetra-, or pentahalogenated aromatic isocyanate comprising reacting a corresponding polyhalogenated phenylamine with an excess of phosgene in the presence of at least about 0.013 mol of tetra (lower alkyl) urea or about 2 mol of tri (lower alkyl) amine per mol of polyhalogenated phenylamine.

2. A method according to claim 1 wherein said reaction is carried out in an inert organic liquid diluent.

3. A process according to claim 1 wherein said tetra (lower alkyl) urea is tetramethylurea.

4. A process according to claim 1 wherein said tri (lower alkyl) amine is triethylamine.

5. The method of claim 1, wherein the polyhalogenated phenylamine is reacted with a saturated solution of phosgene in the presence of from about a 0.015 to 1 mol equivalent of tetra (lower alkyl) urea, and phosgene is continually added throughout the reaction.

6. The method of claim 1, wherein a tetrahalogenated phenylamine is reacted with at least about an 8 mol equivalent of phosgene in the presence of about a 2 mol equivalent of tri (lower alkyl) amine.

7. The method of claim 6, wherein the tri (lower alkyl) amine is triethylamine.

8. The method of claim 5, wherein the tetra (lower alkyl) urea is tetramethyl urea.

* * * * *